United States Patent [19]

DiPippo

[11] 4,042,600
[45] Aug. 16, 1977

[54] PYROLYSIS OF 2-SULFOCHLORIDE BENZOATES

[75] Inventor: Carmine A. DiPippo, Longmeadow, Mass.

[73] Assignee: Scott Paper Company, Philadelphia, Pa.

[21] Appl. No.: 620,281

[22] Filed: Oct. 7, 1975

Related U.S. Application Data

[63] Continuation of Ser. No. 298,226, Oct. 17, 1972, abandoned.

[51] Int. Cl.$^2$ .................. C07D 327/04; C07C 19/02; C07C 25/14
[52] U.S. Cl. .............................. 260/327 S; 260/301; 260/470; 260/471 R; 260/544 N; 260/650 R; 260/652 R
[58] Field of Search ..................................... 260/327 S

[56] References Cited
PUBLICATIONS

Swann, et al., Science & Industrial Reports, Office of the Publication Board, vol. 1, No. 4, (Feb. 1, 1946), Dept. of Comm. (p. 4).

Primary Examiner—Cecilia M. S. Jaisle
Attorney, Agent, or Firm—John W. Kane, Jr.; William J. Foley

[57] ABSTRACT

Ortho-sulfobenzoic anhydride is synthesized by pyrolysis of the 2-sulfochloride benzoates. The benzoate intermediates are readily prepared by reacting either the esters of dithiodibenzoic acid with chloride water or the 2-diazonium chloride benzoates with sulfur dioxide. The invention also provides for the total synthesis of saccharin, free of bitter tasting contaminants, from such reactants, the ultimate step in such synthesis being the ammonolysis of the o-sulfobenzoic anhydride.

10 Claims, No Drawings

PYROLYSIS OF 2-SULFOCHLORIDE BENZOATES

This is a continuation of application Ser. No. 298,226, filed Oct. 17, 1972, and now abandoned.

BACKGROUND OF THE INVENTION

The present invention relates to the pyrolysis of 2-sulfochloride benzoates, and, more especially, relates to the synthesis of o-sulfobenzoic anhydride by pyrolysis of the 2-sulfochloride benzoates in a continuous process and without the formation of undesirable by-products.

In the usual procedure for the synthesis of o-sulfobenzoic anhydride, acid amonium o-sulfobenzoate (conveniently prepared by the acid hydrolysis of saccharin) is reacted with excess thionyl chloride, typically in a toxic organic solvent such as benzene or the aromatic halides, e.g., chlorobenzene. See H. T. Clark and E. E. Dreger, *Org. Syn. Coll. Vol. I*, Second Edition, page 495 (1941). This method, which may be represented as follows:

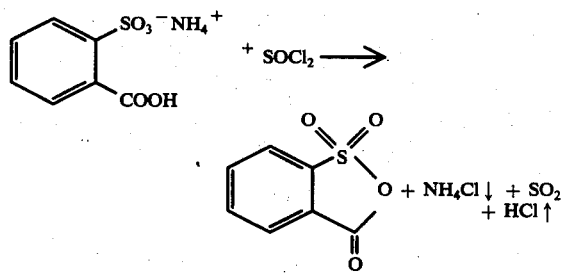

exhibits the disadvantage that the by-product ammonium chloride which precipitates during the course of the reaction must be filtered off from the reaction mixture while it is still hot in order to prevent premature crystallization of the anhydride. And this has proved to be particularly difficult by reason of the noxious fumes evolved. It will be appreciated, therefore, that it is also difficult to attain high yields or large amounts of anhydride product by this method, notably because any crystallized anhydride will be removed along with the precipitated ammonium chloride. Moreover, this process is batch in nature and consequently usually requires a minimum of about one full day for completion.

The more apparently obvious route, namely, that of dehydrating o-sulfobenzoic acid, is not as facile as at first blush the skilled artisan might expect. One method which employs this procedure involves azeotropic removal of water via distillation in relatively elaborate equipment with benzene in the presence of another organic liquid such as isobutyric acid. This alternate synthesis may be represented as follows:

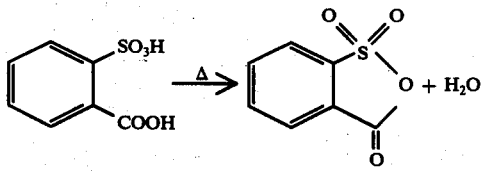

See Belgian Patent No. 629,100.

But, in any event, essentially pure o-sulfobenzoic acid free of cations is exceedingly tedious and difficult to prepare economically. One way to prepare o-sulfobenzoic acid is to start with saccharin; and this method obviously cannot be used for the ultimate synthesis of saccharin.

Ortho-sulfobenzoic anhydride, $C_6H_4COOSO_2$, is a solid having a melting point of 129.5° C., a boiling point of from 184° to 186° C. (18 mm.), and is soluble in hot water, ether, and benzene. It is used as a polymerization inhibitor. But o-sulfobenzoic anhydride is also a useful chemical intermediate and can, for example, be utilized in the manufacture of sulfophthalein indicators and dyes, and saccharin. Saccharin, of course, is variously known as o-benzosulfimide; gluside; benzoylsulfonic imide; and is the anhydride of o-sulfimide benzoic acid having the formula:

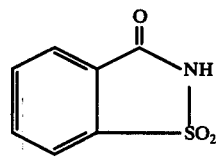

Saccharin is employed in the manufacture of syrups, medicine (substitute for sugar), soft drinks, foods, and the like, and is a nonnutritive sweetener which can readily be converted to sodium or soluble saccharin, and is a white, crystalline powder. It has an exceedingly sweet taste (500 times that of cane sugar), a melting point of about 226° to 230° C., and is soluble in amyl acetate, ethyl acetate, benzene and alcohol; slightly soluble in water, chloroform and ether.

Saccharin has been made from toluene by the following series of reactions:

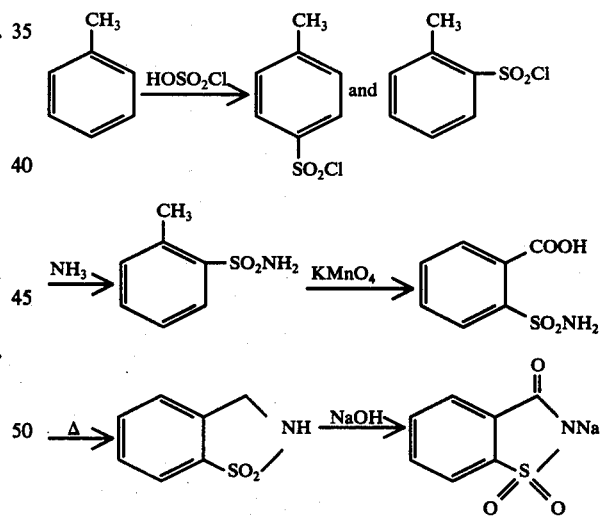

The imide is converted to the sodium salt to increase the solubility in water. Saccharin can also be prepared by converting a mixture of toluene sulfonic acids into the sodium salt, then by distillation with phosphorus trichloride and chlorine to obtain the ortho-toluene sulfonyl chloride, which by means of ammonia is converted into ortho-toluenesulfamide. This is oxidized with permanganate, treated with acid and saccharin crystallized out. It is reported that the slight bitter taste associated with the saccharin prepared by either of the above methods is caused by the presence of o-toluamide. Moreover, the disposal of the p-toluenesulfonyl chloride obtained by-product in the above processes has also been a problem.

Both of these objections have been attempted to be overcome by two or more recent processes, the first [A] commencing with thianaphthene (prepared from styrene and sulfur) and the other [B] with anthranilic acid, as follows [see Noller, *Chemistry of Organic Compounds,* 2nd Edition, pp. 556–557 (1957)]:

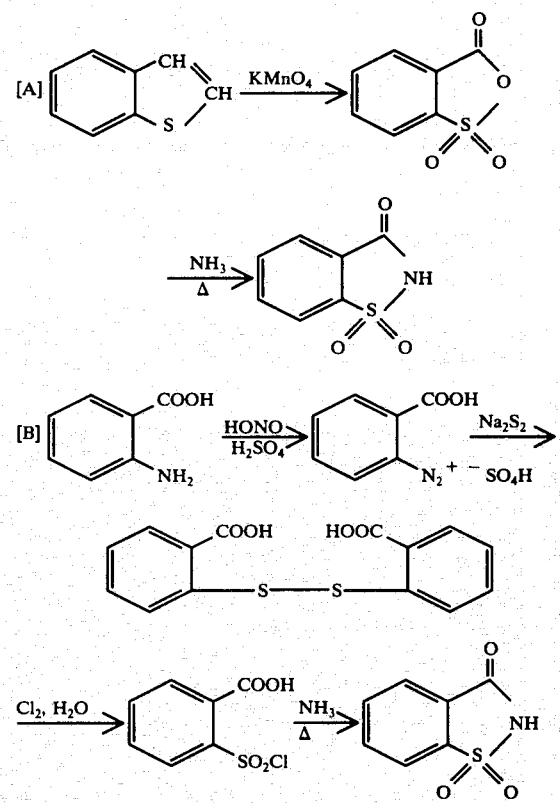

Nevertheless, it too is reported that even when utilizing these alternate routes there still is a slight bitter taste associated with the saccharin, here probably caused by the presence of certain trace contaminants.

SUMMARY OF THE INVENTION

Accordingly, it is an immediate object of this invention to synthesize o-sulfobenzoic anhydride from a 2-sulfochloride benzoate precursor.

Another object of this invention is to provide a method for the synthesis of o-sulfobenzoic anhydride which can be conducted in standard continuous manner without the formation of any undesirable by-products.

Still another object of this invention is to provide an improved method for the total synthesis of saccharin.

Yet another object of this invention is to provide for the total synthesis of saccharin, which recovered saccharin product is free of those bitter tasting contaminants heretofore characterizing the usual saccharin forms.

Another object of this invention is to provide an improved process for the preparation of the s-sulfochloride benzoate intermediates from readily available and inexpensive reactants.

In attaining the objects of this invention, one feature resides in the pyrolysis of various 2-sulfochloride benzoates to yield o-sulfobenzoic anhydride according to the reaction scheme:

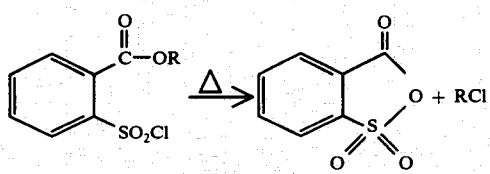

The immediately above reaction may be carried out in the vapor phase by passing the reactant ester through the hot tube and condensing out the product in a continuous fashion. It may also be carried out by heating the reactant ester under reduced pressure and distilling off the product, or by heating the reactant ester alone, or by heating the reactant ester in a suitable high boiling or other solvent, or by pyrolyzing the reactant ester in a sealed tube to aid in trapping the volatile organochloride by-product.

The reactant 2-sulfochloride benzoates an be made easily from starting materials which are readily available. For instance, they may be made by reacting esters of dithiodibenzoic acid with chloride water. They may also be made by reacting 2-diazonium chloride benzoates with sulfur dioxide in the presence of cuprous chloride and acetic acid. 2-Diazonium chloride benzoates can be made by diazotizing esters of anthranilic acid.

Other objects, features, and advantages of this invention will become more apparent from the description which follows.

DETAILED DESCRIPTION OF THE INVENTION

In one embodiment in accordance with this invention, the 2-sulfochloride benzoate precursors are prepared by diazotizing the corresponding anthranilates, advantageously the lower alkyl, e.g., methyl, ethyl or isobutyl, or aralkyl, e.g., benzyl, anthranilates. The diazotizing reaction is conventional and can be effected in standard, known fashion, for example, by treatment, in concentrated hydrochloric acid, with nitric oxides or compounds which release such oxides, e.g., nitrites such as sodium nitrite, or nitrous acid. The resultant 2-diazonium chloride benzoates, useful dye intermediates, are converted into the corresponding 2-sulfochloride benzoate by reaction with sulfur dioxide in the presence of cuprous chloride and acetic acid. Compare Meerwein et al., *Berichte,* 90, 841 (1957).

The foregoing "diazo route" to the 2-sulfochloride benzoates, and wherein the anthranilate starting materials are readily synthesized in known manner from an alcohol and isatoic anhydride, may be represented by the following serious of reactions:

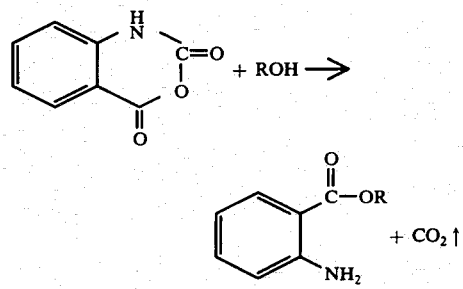

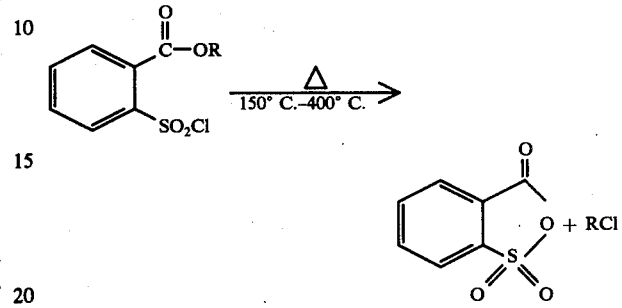

wherein R can be any one of a variety of organic radicals, typically hydrocarbon radicals, inert to the respective reactions, such as lower alkyl and lower cycloalkyl having from 1 to 8 carbon atoms, e.g., methyl, ethyl, n-propyl, i-propyl, n-butyl, i-butyl, sec-butyl, t-butyl, cyclohexyl; aryl having from 6 to 10 carbon atoms, e.g., phenyl; aralkyl wherein the "aryl" and "alkyl" components are as previously defined, e.g., benzyl; and alkenyl having from 2 to 8 carbon atoms, e.g., allyl.

In another and alternate embodiment of this invention, albeit somewhat less facile than the "diazo route", the 2-sulfochloride benzoate precursors are prepared by reacting the corresponding esters of dithiodibenzoic acid, advantageously dibenzyl dithiodibenzoate, with chloride water.

The foregoing "dithio route" to the 2-sulfochloride benzoates, and wherein the dithiodibenzoate starting materials (useful in and of themselves as antioxidants and rubber accelerators) are also readily synthesized in known manner from an alcohol and dithiodibenzoyl dichloride, may be represented by the following series of reactions:

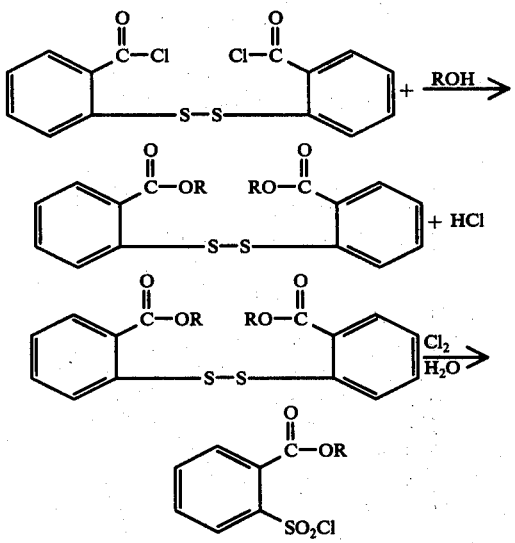

wherein R is as heretofore defined.

Pyrolysis of the subject 2-sulfochloride benzoates according to the invention, whether prepared via the aforesaid "diazo route" or "dithio route", or any other route whatsoever, advantageously takes place at a temperature in the range of from about 150° to about 400° C., albeit there exist certain preferred values within this range for the pyrolysis of a given ultimate species, e.g., about 165° C. for pyrolysis of either isopropyl or benzyl 2-sulfochloride benzoate, and about 225° C. for pyrolysis of isobutyl 2-sulfochloride benzoate. And, as heretofore mentioned, the following pyrolysis reaction of the invention:

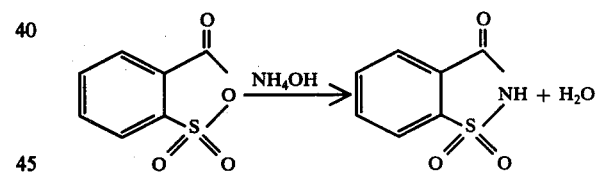

wherein R is as previously defined, exhibits the advantages over the known prior art in that this reaction may easily be carried out continuously, the same does not involve the formation of such by-products as ammonium chloride which makes isolation of the desired anhydride difficult, the pyrolysis does not require the use of undesirable reagents such as thionyl chloride or toxic solvents such as benzene or chlorobenzene, and the product o-sulfobenzoic anhydride can be directly obtained in high yields and in a relatively pure state.

The o-sulfobenzoic anhydride produced according to the invention by pyrolysis of the 2-sulfochloride benzoates is readily converted into essentially pure saccharin free of bitter tasting contaminants by simple ammonolysis, for example, by ammonolysis with a concentrated solution of ammonium hydroxide, namely:

In order to further illustrate the present invention and the advantages thereof, the following specific examples are given, it being understood that the same are intended merely as illustrative and in no wise limitative.

EXAMPLE 1

Pyrolysis of Isobutyl-2-Sulfochloride Benzoate Prepared Via "Diazo Route"

A slurry of 96.6 g. of isobutyl anthranilate (prepared by reaction of isobutyl alcohol with isatoic anhydride) in 170 ml. of concentrated HCl was diazotized at a temperature of less than 10° C. with a 40% aqueous solution of sodium nitrite until an end-point was reached with Green Reagent.

This reaction mixture was then filtered through a fritted glass filter and the cold filtrate poured into a cold mixture consisting of 191 g. of sulfur dioxide and 6.6 g. of cuprous chloride in 400 ml. of glacial acetic acid. This reaction mixture was removed from the ice bath and allowed to warm up to 35° C.; much evolution of gas was observed.

The above reaction mixture was then poured into 2-liters of water, causing the separation of a light brown liquid. This mixture was extracted with 500 ml. of methylene chloride. The organic phase was separated, washed three times with 250 ml. portions of 5% sodium bicarbonate, and dried with anhydrous magnesium sulfate. After filtering off the drying agent and removing the solvent under vacuum with a rotary evaporator, Rota-Vap, 76 g. of crude product remained, namely, isobutyl-2-sulfochloride benzoate.

Attempted vacuum distillation of the crude product produced three fractions as the pot temperature gradually rose and distillation proceeded:

Fraction I — b.p. = 79° C./1.4 mm. Gas chromatographic analysis showed this liquid to be mostly homogeneous isobutyl-2-sulfochloride benzoate.

Fraction II — b.p. = 96.5° C./2mm. Pot temp. = 213° C. A small amount of white solid (o-sulfobenzoic anhydride) formed in the liquid distillate. G.C. analysis showed this fraction to consist of a mixture of o-sulfobenzoic anhydride and isobutyl-2-sulfochloride benzoate.

Fraction III — b.p. = 125° C./3 mm. Pot temp. = 220° C. The distillate was solid o-sulfobenzoic anhydride which solidified in the condenser and was positively identified by comparative infra-red analysis.

EXAMPLE 2

Pyrolysis of Benzyl-2-Sulfochloride Benzoate Prepared Via "Dithio Route"

In a 3-necked 1-liter flask equipped with overhead stirrer, thermometer, gas inlet tube and ice-water bath there was placed 200 ml. of water and a solution of 24.3 (0.05 moles) of dibenzyl dithiodibenzoate dissolved in 200 ml. of chloroform. (The dibenzyl dithiodibenzoate was prepared by reaction of dithiodibenzoyl dichloride with benzyl alcohol.) Chlorine gas was bubbled into this mixture was vigorous stirring and at an arbitrary rate. The temperature rose from 5° 1 to 12° C.; after 20 – 25 min. the temperature dropped back to 5° C. and the reaction was stopped.

The reaction mixture was transferred to a separatory funnel and the upper water layer discarded. The organic layer was dried with anhydrous magnesium sulfate. After filtering off the drying agent and removing the solvent on a Rota-Vap, the resultant crude benzyl-2-sulfochloride benzoate was vacuum distilled. Pure o-sulfobenzoic anhydride distilled off: b.p. = 110° C./0.3 mm; Pot temp. = 188° 1 C. Benzyl chloride was detected in the dry ice vapor trap by gas chromatographic analysis.

EXAMPLE 3

Ammonolysis of O-Sulfobenzoic Anhydride

The resultant o-sulfobenzoic anhydride prepared according to either of the preceeding examples was cooled to 50° C. until the anhydride solidified. A concentrated solution (28%) of ammonium hydroxide was slowly added thereto and the mixture stirred at 50° C. for 2 to 3 hours; thereafter the reaction mixture was cooled and filtered, and the saccharin was recovered therefrom in essentially pure state, free of bitter tasting contaminants.

Thus, it will be appreciated that the instant invention provides not only an improved method for the synthesis of o-sulfobenzoic anhydride by pyrolysis of the 2-sulfochloride benzoates without the formation of undesirable by-products, advantageously conducted continuously but also an improved method wherein the by-product organochlorides themselves are of significant commercial worth. For example, in the pyrolysis of methyl-2-sulfochloride benzoate, the by-product methyl chloride itself is a valuable refrigerant composition; and in the pyrolysis of benzyl-2-sulfochloride benzoate, the by-product benzyl chloride is a useful pharmaceutical intermediate. Similarly, the "R" function in the ester moiety of the 2-sulfochloride benzoates can be tailored specifically with a view towards concomitant preparation, together with the desired anhydride, of a certain RCl.

The above examples and disclosures are set forth merely for illustrating the mode and manner of the invention. And, while various modifications and embodiments can be made by those skilled in the art, in the light of this invention, such as introducing various substituents on the benzene basic nucleus of the subject benzoic compounds, or employing a bromide or other halide reactant in the pyrolysis rather than the corresponding chloride, they are made without departing from the spirit of the invention.

What is claimed is:

1. The method for the synthesis of ortho-sulfobenzoic anhydride which comprises pyrolyzing a 2-sulfochloride benzoate at elevated temperatures.

2. The method as defined in claim 1, wherein the pyrolysis is conducted at a temperature in the range of from between about 150° and about 400° C.

3. The method as defined in claim 1, wherein the reactant 2-sulfochloride benzoate has the structural formula:

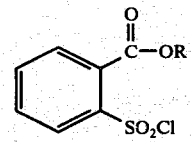

wherein R is an organic moiety inert to the pyrolysis reaction.

4. The method as defined by claim 3, wherein R is a hydrocarbon.

5. The method as defined by claim 4, wherein R is selected from the group consisting of lower alkyl and lower cycloalkyl having from 1 to 8 carbon atoms; aryl having from 6 to 10 carbon atoms; aralkyl, with the alkyl and aryl components thereof as previously defined; and alkenyl having from 2 to 8 carbon atoms.

6. The method as defined in claim 5, wherein R is selected from the group consisting of methyl, ethyl, n-propyl, i-propyl, n-butyl, i-butyl, sec-butyl, tert-butyl and benzyl.

7. The method as defined by claim 1, wherein the 2-sulfochloride benzoate is pyrolyzed and the o-sulfobenzoic anhydride is recovered in continuous fashion.

8. The method for the preparation of an organochloride having the formula RCl, which comprises pyrolyzing at elevated temperatures a 2-sulfochloride benzoate having the structural formula:

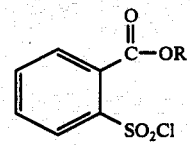

wherein R is an organic moiety inert to the pyrolysis reaction, and thence recovering said organochloride from the pyrolysis mixture.

9. The method as defined in claim 8, wherein the 2sulfochloride benzoate pyrolyzed is selected from the group consisting of methyl, ethyl, n-propyl, isopropyl, n-butyl, isobutyl, sec-butyl, tert-butyl and benzyl 2-sulfochloride benzoate.

10. The method for the synthesis of ortho-sulfobenzoic anhydride which comprises pyrolyzing a 2-sulfohalide benzoate at elevated temperatures.

* * * * *